US010398040B1

(12) United States Patent
Vinciarelli

(10) Patent No.: US 10,398,040 B1
(45) Date of Patent: Aug. 27, 2019

(54) POWER ADAPTER PACKAGING

(71) Applicant: VLT, Inc., Sunnyvale, CA (US)

(72) Inventor: Patrizio Vinciarelli, Boston, MA (US)

(73) Assignee: VLT, Inc., Andover, MA (US)

( * ) Notice: Subject to any disclaimer, the term of this patent is extended or adjusted under 35 U.S.C. 154(b) by 0 days.

(21) Appl. No.: 15/972,092

(22) Filed: May 4, 2018

Related U.S. Application Data

(63) Continuation of application No. 14/596,848, filed on Jan. 14, 2015, now Pat. No. 9,967,984.

(51) Int. Cl.
| | |
|---|---|
| *H05K 5/00* | (2006.01) |
| *H05K 7/14* | (2006.01) |
| *H05K 5/04* | (2006.01) |
| *H05K 1/14* | (2006.01) |

(52) U.S. Cl.
CPC ............ *H05K 5/0069* (2013.01); *H05K 1/14* (2013.01); *H05K 1/141* (2013.01); *H05K 1/142* (2013.01); *H05K 1/145* (2013.01); *H05K 5/0008* (2013.01); *H05K 5/04* (2013.01); *H05K 7/1432* (2013.01); *H05K 2201/068* (2013.01)

(58) Field of Classification Search
CPC ........ H05K 5/0069; H05K 1/14; H05K 1/141; H05K 1/142; H05K 1/145; H05K 5/0008; H05K 5/04; H05K 7/1432
See application file for complete search history.

(56) References Cited

U.S. PATENT DOCUMENTS

| | | | |
|---|---|---|---|
| 4,366,342 A | 12/1982 | Breedlove | |
| 4,551,747 A | 11/1985 | Gilbert et al. | |
| 5,027,255 A | 6/1991 | Zeitlin | |
| 5,241,133 A | 8/1993 | Mullen et al. | |

(Continued)

FOREIGN PATENT DOCUMENTS

| | | |
|---|---|---|
| EP | 0715322 | 4/1998 |
| WO | WO 1995/027308 | 10/1995 |
| WO | WO 2012/155036 | 11/2012 |

OTHER PUBLICATIONS

AFM Microelectronics Inc., "General Purpose Capacitors," www.afmmicroelectronics.com, 14 pages, published on or before Jul. 26, 2010.

(Continued)

*Primary Examiner* — Binh B Tran
*Assistant Examiner* — Douglas R Burtner
(74) *Attorney, Agent, or Firm* — Fish & Richardson P.C.

(57) ABSTRACT

A power adapter package comprises a power conversion module, an input board assembly comprising terminals for receiving power from an input source and delivering power to the input of the power conversion module, an output board assembly for receiving power from the output of the power conversion module and delivering power to a load via output terminations, a signal isolator comprising a bridge board spanning a distance between the input board and the output board, a case comprising top and bottom covers, and end cap assemblies for supporting and insulating input and output terminations. The bridge board may comprise a multilayer substrate comprising galvanically isolated and magnetically coupled transformer windings. The input and output boards may be soldered to contacts formed along a peripheral edge of the power conversion module.

8 Claims, 17 Drawing Sheets

(56) References Cited

U.S. PATENT DOCUMENTS

| | | | |
|---|---|---|---|
| 5,481,436 A | 1/1996 | Werther | |
| 5,728,600 A | 3/1998 | Saxelby, Jr. et al. | |
| 5,864,092 A * | 1/1999 | Gore | H01L 23/49805 |
| | | | 174/260 |
| 5,952,909 A | 9/1999 | Umeno et al. | |
| 6,073,339 A | 6/2000 | Levin | |
| 6,147,876 A * | 11/2000 | Yamaguchi | H01L 23/24 |
| | | | 257/698 |
| 6,262,600 B1 | 7/2001 | Haigh et al. | |
| 6,403,009 B1 | 6/2002 | Saxelby, Jr. et al. | |
| 6,501,364 B1 | 12/2002 | Hui et al. | |
| 6,717,820 B1 * | 4/2004 | Loh | H01L 31/0203 |
| | | | 257/E31.118 |
| 6,765,469 B2 * | 7/2004 | Sortor | H01F 19/04 |
| | | | 336/200 |
| 6,830,959 B2 | 12/2004 | Estacio | |
| 6,888,438 B2 | 5/2005 | Hui et al. | |
| 6,940,013 B2 | 9/2005 | Vinciarelli et al. | |
| 7,283,345 B2 | 10/2007 | Liu | |
| 7,361,844 B2 | 4/2008 | Vinciarelli et al. | |
| 7,468,547 B2 | 12/2008 | Harvey | |
| 7,701,731 B2 | 4/2010 | Dhuyvetter et al. | |
| 7,741,943 B2 | 6/2010 | Fouquet et al. | |
| 7,768,371 B2 | 8/2010 | Hui et al. | |
| 7,915,992 B2 | 3/2011 | de Rooij et al. | |
| 7,972,143 B2 | 7/2011 | Smejtek | |
| 8,188,806 B2 | 5/2012 | Ho et al. | |
| 8,344,842 B1 * | 1/2013 | Luzanov | H05K 1/141 |
| | | | 336/192 |
| 8,385,043 B2 | 2/2013 | Ng et al. | |
| 8,427,269 B1 | 4/2013 | Vinciarelli | |
| 8,592,944 B2 | 11/2013 | Santangelo et al. | |
| 8,896,111 B2 | 11/2014 | Vinciarelli | |
| 8,963,676 B1 | 2/2015 | Hoang | |
| 10,264,670 B2 * | 4/2019 | Oh | H05K 1/028 |
| 2002/0096348 A1 | 7/2002 | Saxelby et al. | |
| 2003/0058628 A1 | 3/2003 | Boylan | |
| 2003/0095026 A1 | 5/2003 | Kawanobe | |
| 2004/0100778 A1 | 5/2004 | Vinciarelli et al. | |
| 2005/0101188 A1 | 5/2005 | Benham | |
| 2005/0184381 A1 * | 8/2005 | Asahi | H01R 13/2414 |
| | | | 257/693 |
| 2006/0133041 A1 | 6/2006 | Belady | |
| 2006/0133042 A1 | 6/2006 | Belady | |
| 2007/0158799 A1 * | 7/2007 | Chiu | H01L 23/49805 |
| | | | 257/678 |
| 2007/0241440 A1 | 10/2007 | Hoang et al. | |
| 2008/0311771 A1 * | 12/2008 | Cho | H01R 12/57 |
| | | | 439/74 |
| 2009/0156913 A1 * | 6/2009 | MacNeish, III | A61B 5/14552 |
| | | | 600/310 |
| 2009/0251873 A1 * | 10/2009 | Cheng | H05K 3/3442 |
| | | | 361/767 |
| 2010/0197150 A1 | 8/2010 | Smejtek | |
| 2010/0246152 A1 | 9/2010 | Lin et al. | |
| 2011/0050292 A1 | 3/2011 | Hui et al. | |
| 2011/0104919 A1 | 5/2011 | Vinciarelli | |
| 2011/0116236 A1 * | 5/2011 | Akahori | H05K 1/141 |
| | | | 361/704 |
| 2012/0073864 A1 * | 3/2012 | Stefanoff | H05K 1/142 |
| | | | 174/252 |
| 2012/0287582 A1 | 11/2012 | Vinciarelli et al. | |
| 2013/0164952 A1 * | 6/2013 | Wu | H05K 1/142 |
| | | | 439/62 |
| 2013/0223038 A1 * | 8/2013 | Yamamoto | H01L 25/16 |
| | | | 361/807 |
| 2014/0102626 A1 * | 4/2014 | Clayton | H05K 3/363 |
| | | | 156/196 |
| 2014/0218155 A1 * | 8/2014 | Akre | H05K 1/141 |
| | | | 336/192 |
| 2014/0355218 A1 | 12/2014 | Vinciarelli et al. | |
| 2016/0150646 A1 * | 5/2016 | Oh | H05K 1/14 |
| | | | 361/749 |
| 2016/0174376 A1 * | 6/2016 | Oh | H05K 1/118 |
| | | | 361/749 |
| 2016/0365795 A1 | 12/2016 | Madsen | |

OTHER PUBLICATIONS

Analog Devices, "ADM2490E: 5 kV Signal Isolated, High Speed (16 Mbps), ESD Protected, Full Duplex RS-485 Transceiver", 2 pages, downloaded Sep. 30, 2011.

Analog Devices, "High Speed, ESD-Protected, Full-Duplex, iCoupler Isolated RS-485 Transceiver", 16 pages, 2006-2008.

Analog Devices, "iCoupler® Digital Isolation—Unparalleled Performance and Integration", downloaded Aug. 31, 2011.

Application Notes, Connectors for LED Lighting Applications, Mill-Max Mfg. Corp., Jun. 20, 2014.

Avago Technologies, "ACML-7400, ACML-7410 and ACML-7420 3.3V/5V 100 MBd High Speed CMOS Digital Isolator", 13 pages, May 16, 2011.

Avago Technologies, "Parametric Search: digital Isolator", 2 pages, 2005-2011.

Bhat, Shriram N., et al., "Enhancement of Via Integrity in High-Tg Multilayer Printed Wiring Boards," Feb. 19, 2013, IEEE, 7 pgs.

Business Wire, "Analog Devices Introduces First Digital Isolator Packaging that Meets Safety Requirements in Medical and Industrial Applications", www.businesswire.com/news/home/20111005005026/en/anaglog-Devices-Introduc . . . , 3 pages, Oct. 12, 2011.

Edge Mount Q-Strip/Q-PAIRS Interconnects Application Overview, TecTalk, Samtec, Inc. Dec. 2012.

GradConn, "Planar board to board connectors," accessed online http://gradconn.com/right-angle/board-connectors.asp Jun. 20, 2014.

Hui et al., "Optimal Operation of Coreless PCB Transformer-Isolated Gate Drive Circuits with Wide Switching Frequency Range," IEEE Transactions on Power Electronics, vol. 14, No. 3, 506-514, May 1999.

Hui et al., "Some Electromagnetic Aspects of Coreless PCB Transformers", IEEE Transactions on Power Electronics, vol. 15, No. 4, pp. 805-810, Jul. 2000.

Ideas for attaching / connecting / stacking one PCB onto another with no gap; http://electronics.stackexchange.com/questions/45733/ideas-for -attaching-connecting-stacking-one-PCB-onto-another-with-no-gap; accessed on Jun. 3, 2015; 5 pages.

International Search Report and Written Opinion, PCT/US2012/37495, dated May 6, 2013, 18 pages.

Isolator vs. Optocoupler Technology, Silicon Labs, downloaded Feb. 22, 2013, 21 pages, www.silabs.com/products/power/isolators.

Kahn, "Technical Information: Multilayer Ceramic Capacitors—Materials and Manufacture," Microelectronics Inc., 8 pages, published on or before Jul. 26, 2010.

Lee et al., "Multilayer Stacked Coreless Printed Spiral Winding Inductor With Wide Frequency Bandwidth", IEEE Energy Conversion Congress and Exposition, pp. 1002-1009, 2009.

Minteer, Design of a New Transformer-Isolated Analog Acquisition System, IEEE Transactions on Power Delivery vol. 24, No. 3, pp. 1054-1062, Jul. 2009.

Mohan et al., "Power Electronics—Converters, Applications and Design", 2nd Edition, John Wiley and Sons, pp. 708-709, 1995.

NVE Corporation, "Isolator Product Application", 3 pages downloaded Sep. 30, 2011.

NVE Corporation, IL600 Series, 21 pages, Sep. 2010.

One Piece Card Edge, Series 9159, AVX, Jun. 12, 2014.

Silicon Labs, "Discrete ISOvolt-EVB", 14 pages, Rev. 02 Sep. 2011.

Silicon Labs, "SI8410/20/21", 30 pages, Mar. 2011.

Silicon Labs, "Si84xx Digital Isolators", downloaded Sep. 30, 2011.

Tang et al., "Evaluation of the Shielding Effects on Printed-Circuit-Board Transformers Using Ferrite Plates and Copper Sheets", IEEE Transactions on Power Technology, vol. 17, No. 6, pp. 1080-1088, Nov. 2002.

(56) References Cited

OTHER PUBLICATIONS

Texas Instruments, "Application Report ISO72x Digital Isolator Magnetic-Field Immunity", 6 pages Jan. 2006—Revised Feb. 2006.

* cited by examiner

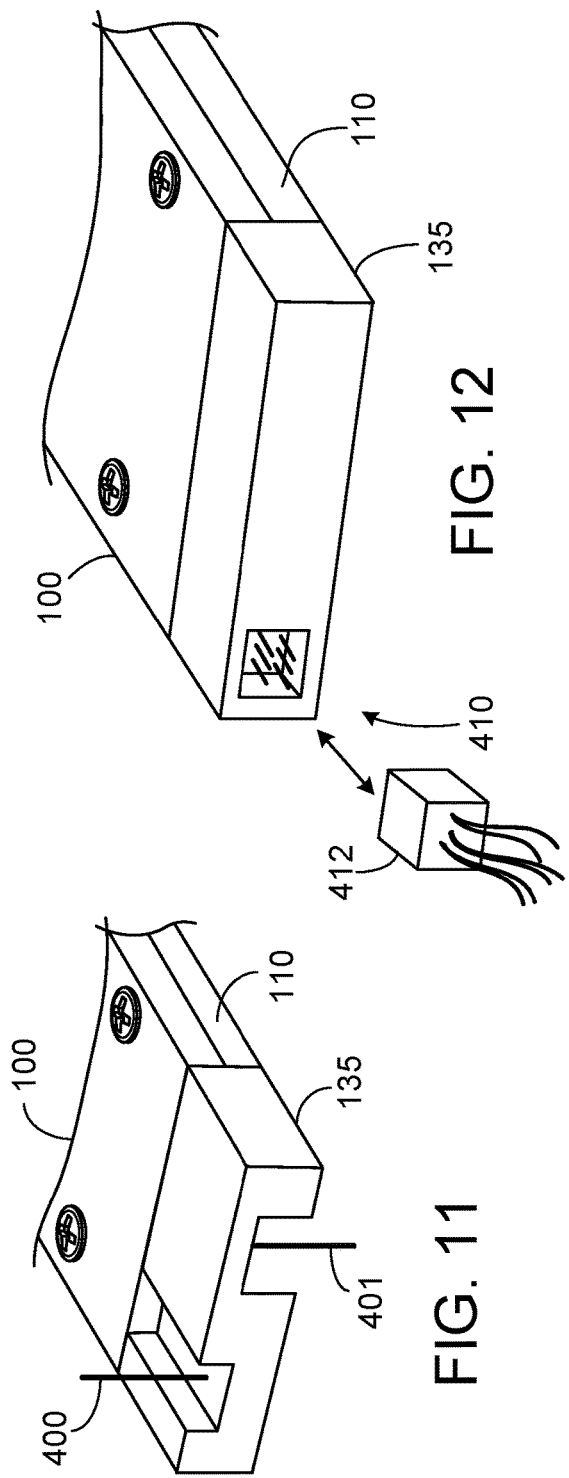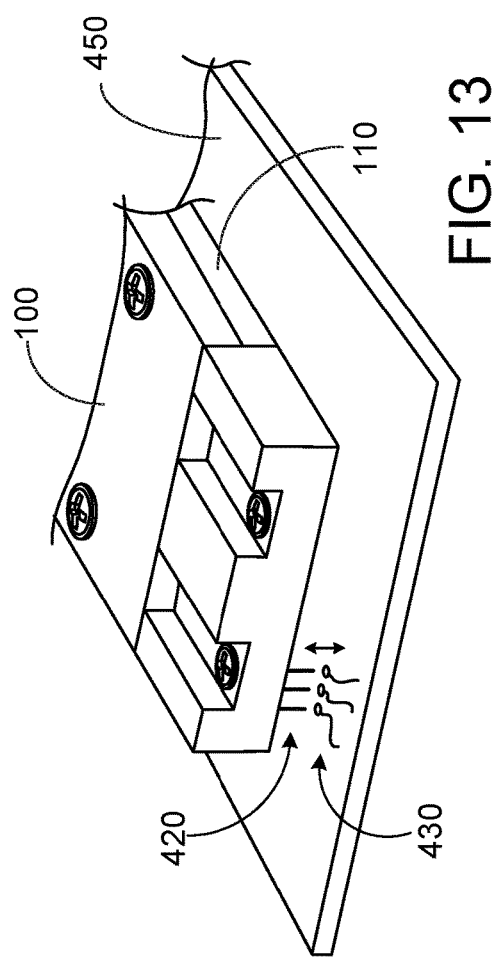

POWER ADAPTER PACKAGING

CROSS-REFERENCE TO RELATED APPLICATION

This application is a continuation application of U.S. patent application Ser. No. 14/596,848, filed on Jan. 14, 2015, which is related to U.S. patent application Ser. No. 14/596,836, titled "Isolator With Integral Transformer," filed on Jan. 14, 2015, now U.S. Pat. No. 9,508,485, issued on Nov. 29, 2016 and U.S. patent application Ser. No. 14/596,914, titled "Method of Forming an Electrical Connection to an Electronic Module," filed on Jan. 14, 2015, now U.S. Pat. No. 9,936,580, issued on Apr. 3, 2018. The above applications and patents are incorporated herein by reference.

TECHNICAL FIELD

This invention describes apparatus and methods for packaging power conversion assemblies.

BACKGROUND

Power conversion modules widely available as self-contained modular assemblies are typically intended to be used as components in larger power systems. A power conversion module may be an AC-DC or DC-DC power converter and is typically available in a wide variety of electrical ratings within a custom and standardized package configuration. Consider, for example, that a family of power conversion modules may be offered in a standard mechanical package having either identical or very similar physical dimensions with identical or similar lead arrangements. One power conversion module in the family may be configured to receive power at an input voltage of 48 VDC and produce a 5 VDC output at a specified maximum power level, while another module in the family, available in the same mechanical package with identical or similar lead configurations, may be configured to receive power at the same (48 VDC) or different (e.g. 300 VDC) input voltage and produce the same (5 VDC) or different (12 VDC) output voltage. Power system designers may combine power conversion modules from the same or different families with or without additional circuitry to create an application-specific power system. Such power conversion modules are commercially available in various form factors and power levels. Examples of power conversion modules include Vicor HD Brick, VI Chip, and CHiP modules (manufactured by Vicor Corporation, Andover, Mass., USA, www.vicorpower.com).

Galvanic isolation between input and output is often required in power systems, particularly in systems converting power received from utilities. Isolation may be used for safety, e.g., to isolate selected portions of a circuit from high voltages in another part of a circuit, and/or they may be used to minimize or prevent disturbances in one portion of a circuit that might otherwise be caused by normal-mode or common-mode signals in another part of a circuit. Signal isolators may be used to pass control signal or status information between the input and output of an isolated power adapter. Many types of digital and analog signal isolators are known that use optical, magnetic, or capacitive mediums for communicating across an isolation boundary.

SUMMARY

In general, in one aspect, an apparatus for converting power received from an input source for delivery to a load is provided. The apparatus includes a first printed circuit board ("PCB") having electrical terminations adapted for connection to the input source; a second PCB having electrical terminations for connection to the load; a power conversion module ("PCM") having a module input electrically connected to the first PCB, a module output electrically connected to the second PCB, and power conversion circuitry adapted to convert power between the module input and the module output; and an isolator board having first terminations electrically connected to the first PCB and second terminations electrically connected to the second PCB, the first terminations being galvanically isolated from the second terminations. The first PCB is separated from the second PCB, and the isolator board forms a bridge between the first and second PCBs.

Implementations of the apparatus may include one or more of the following features. The PCM can further include an internal PCB having a first vertical edge including one or more surface contacts and a second vertical edge having one or more surface contacts, the first and second vertical edges forming a portion of first and second vertical edges of the power conversion module; and wherein the bridge board can be arranged at an angle relative to the internal, first, and second PCBs. The angle can be a right angle. The apparatus can further include at least one end cap assembly having a non-conductive body and a plurality of electrically conductive terminals connected to either the first or second PCB. The apparatus of claim 4 wherein the at least one end cap assembly further comprises a first end cap assembly having a plurality of electrically conductive terminals electrically connected to the first PCB and adapted for carrying power between the input source and the first PCB and a second end cap assembly having a plurality of electrically conductive terminals connected to the second PCB and adapted for carrying power between an output of the second PCB and the load. The terminals can include screw threads for receiving a mating screw. The terminals can include pins for mating with respective terminations on an external PCB. At least one of the first or second end cap assemblies can further include additional terminations for making electrical signal connections with the respective first or second PCB. The additional terminations can be provided in a connector adapted to receive a mating connector assembly. The additional terminations can be provided as pins adapted to mate with respective terminations on a PCB.

In general, in another aspect, an apparatus for converting power received from an input source for delivery to a load is provided. The apparatus includes a first printed circuit board ("PCB") having electrical terminations adapted for connection to the input source; a second PCB having electrical terminations for connection to the load; and a power conversion module ("PCM") having a module input electrically connected to the first PCB, a module output electrically connected to the second PCB, and power conversion circuitry adapted to convert power between the module input and the module output. At least one of the electrical connections from the module input or module output and the respective first PCB or second PCB includes a solder connection formed between a conductive area located on a vertical edge of the respective PCB and a conductive area located on a vertical edge of the power conversion module, wherein the vertical edges are approximately parallel to each other and the connection is located at an elevation below a top surface and above a bottom surface of the power conversion module.

Implementations of the apparatus may include one or more of the following features. The PCM can further include an internal PCB having a first vertical edge including one or more surface contacts and a second vertical edge having one or more surface contacts, the first and second vertical edges forming a portion of first and second vertical edges of the power conversion module. The internal PCB can be generally parallel to the first and second PCBs. The apparatus can include a housing having a first coefficient of thermal expansion; wherein the PCM can include an internal PCB having a second coefficient of thermal expansion; and wherein the first coefficient of thermal expansion can approximate the second thermal coefficient of expansion. The apparatus can further include a mechanical connection between the housing and a surface of the PCM adapted to force the housing and the PCM to expand or contract in substantially equal measures in a direction between the module input and the module output. The mechanical connection can include a structural epoxy bond formed at a build temperature selected to pre-bias the mechanical stress between the PCM and the housing. The build temperature can be near the middle of a specified temperature range for the apparatus. The build temperature can be near an end of a specified temperature range for the apparatus. The apparatus can further include at least one end cap assembly having a non-conductive body and a plurality of electrically conductive terminals connected to either the first or second PCB. The at least one end cap assembly can further include a first end cap assembly having a plurality of electrically conductive terminals electrically connected to the first PCB and adapted for carrying power between the input source and the first PCB and a second end cap assembly having a plurality of electrically conductive terminals connected to the second PCB and adapted for carrying power between an output of the second PCB and the load. The terminals can include screw threads for receiving a mating screw. The terminals can include pins for mating with respective terminations on an external PCB. At least one of the first or second end cap assemblies can further include additional terminations for making electrical signal connections with the respective first or second PCB. The additional terminations can be provided in a connector adapted to receive a mating connector assembly. The additional terminations can be provided as pins adapted to mate with respective terminations on a PCB.

In general, in another aspect, an apparatus for converting power received from an input source for delivery to a load is provided. The apparatus includes a first printed circuit board ("PCB") having electrical terminations adapted for connection to the input source and electrical terminations for connection to the load; and a power conversion module ("PCM") having a module input and a module output, each being electrically connected to the first PCB, and power conversion circuitry adapted to convert power between the module input and the module output. At least one of the electrical connections from the module input or module output and the first PCB includes a solder connection formed between a conductive area located on a vertical edge of the PCB and a conductive area located on a vertical edge of the power conversion module, wherein the vertical edges are approximately parallel to each other and the connection is located at an elevation below a top surface and above a bottom surface of the power conversion module.

DESCRIPTION OF DRAWINGS

FIGS. 11, 12 and 13 show various termination schemes.

DETAILED DESCRIPTION

Figure 1:
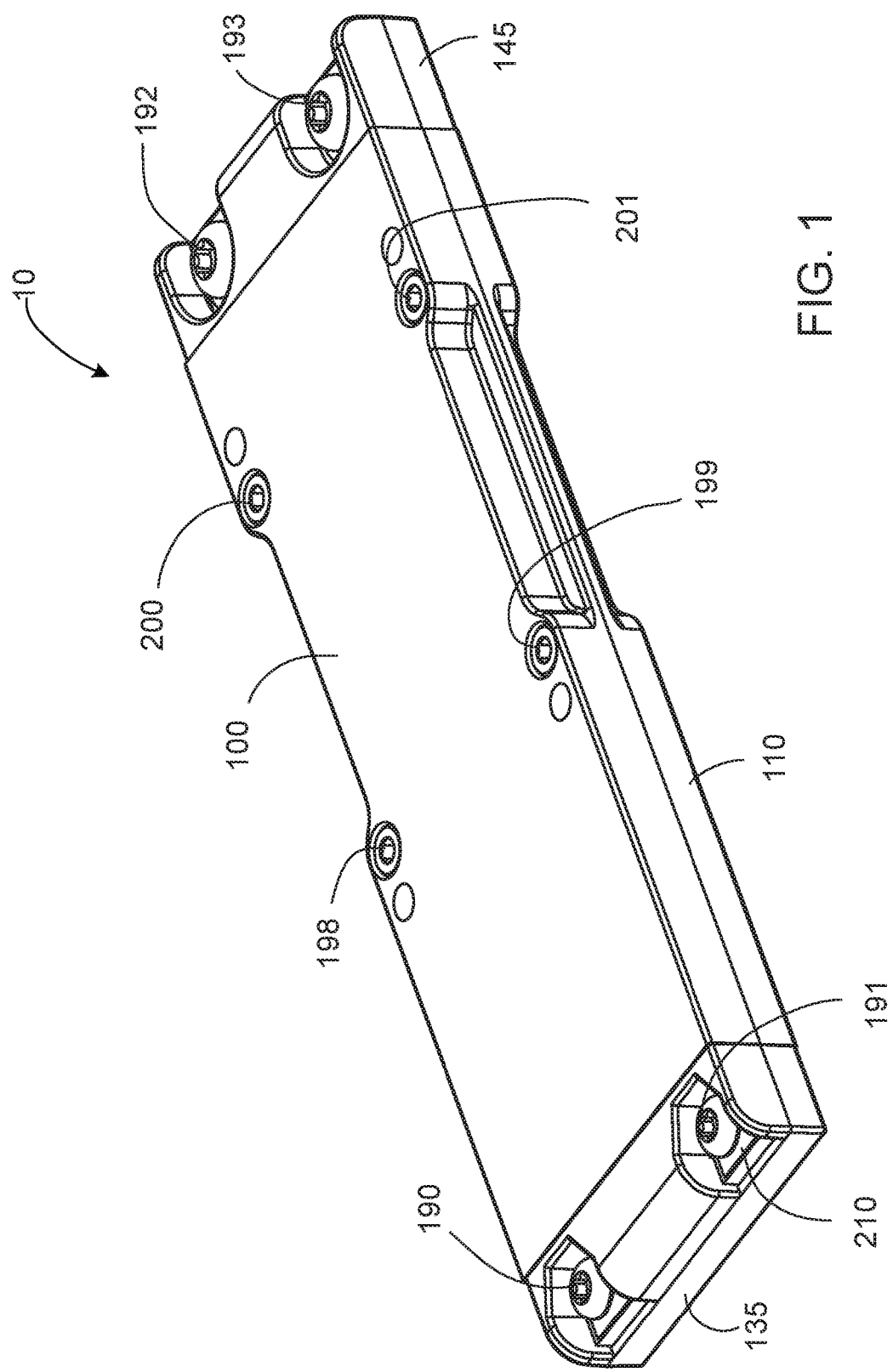
FIG. 1 shows a top perspective view of a packaged power adapter.

FIG. 1 shows a perspective view of an assembled power adapter 10. The power adapter may, e.g., receive an input from an AC and/or DC electrical source (not shown) and may deliver an output to a load (also not shown); the output may be regulated and/or scaled in magnitude relative to the input. As used herein, a power adapter is a packaged power system that comprises a power conversion module, input terminations for making connections to and receiving power from an input source, output terminations for making connections to and delivering power to a load, and optional input circuitry for, e.g., processing and filtering power received from the input source (e.g., noise and transient filtering circuitry, power factor correction circuitry) and delivering power to the input of the power conversion module, and/or output circuitry for processing power received from the power conversion module (e.g., noise filtering circuitry, filter capacitors, supervisory circuitry) and delivering power to the load.

Figure 2:
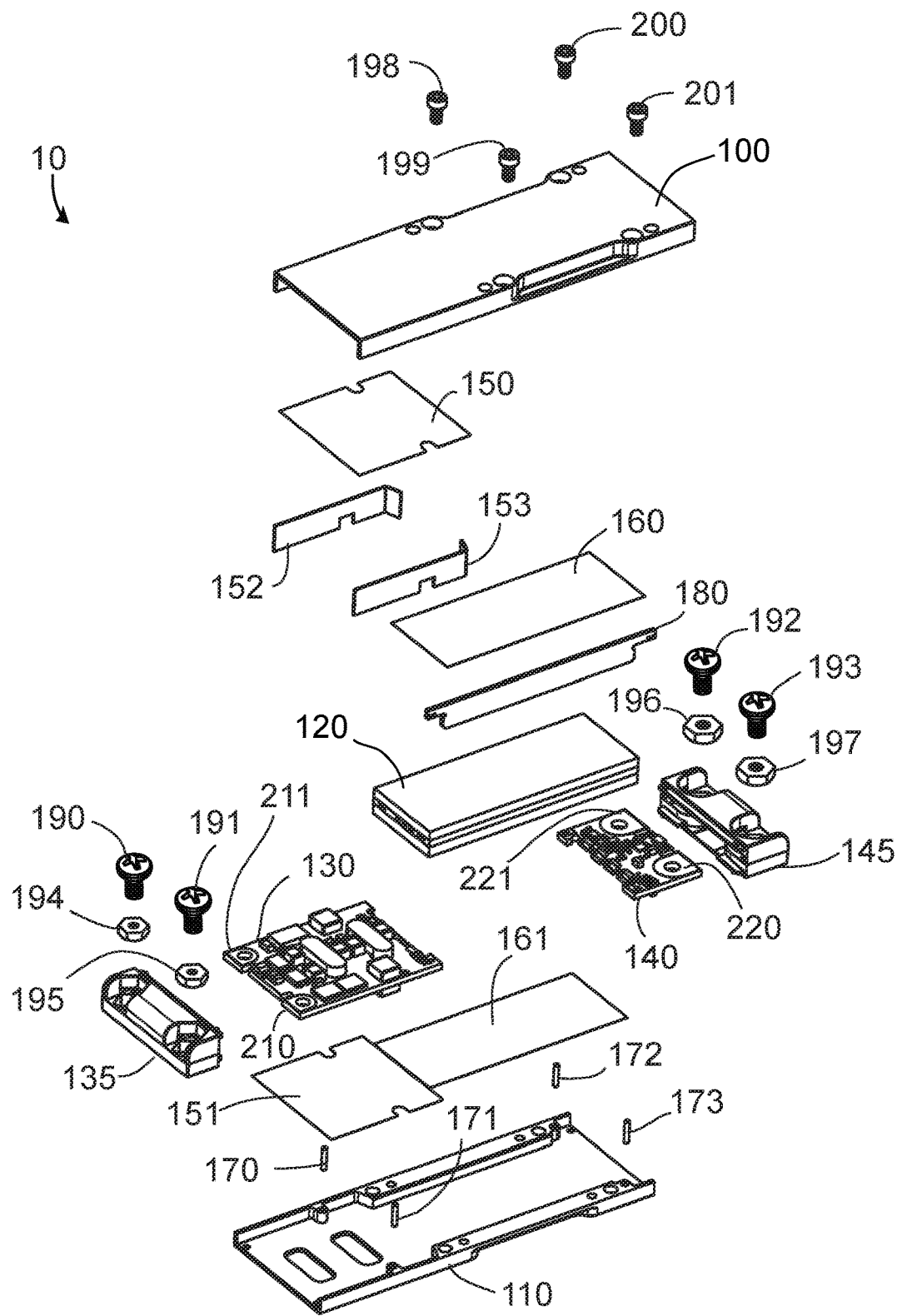
FIG. 2 shows an exploded perspective view of the adapter of FIG. 1.
Figure 3:
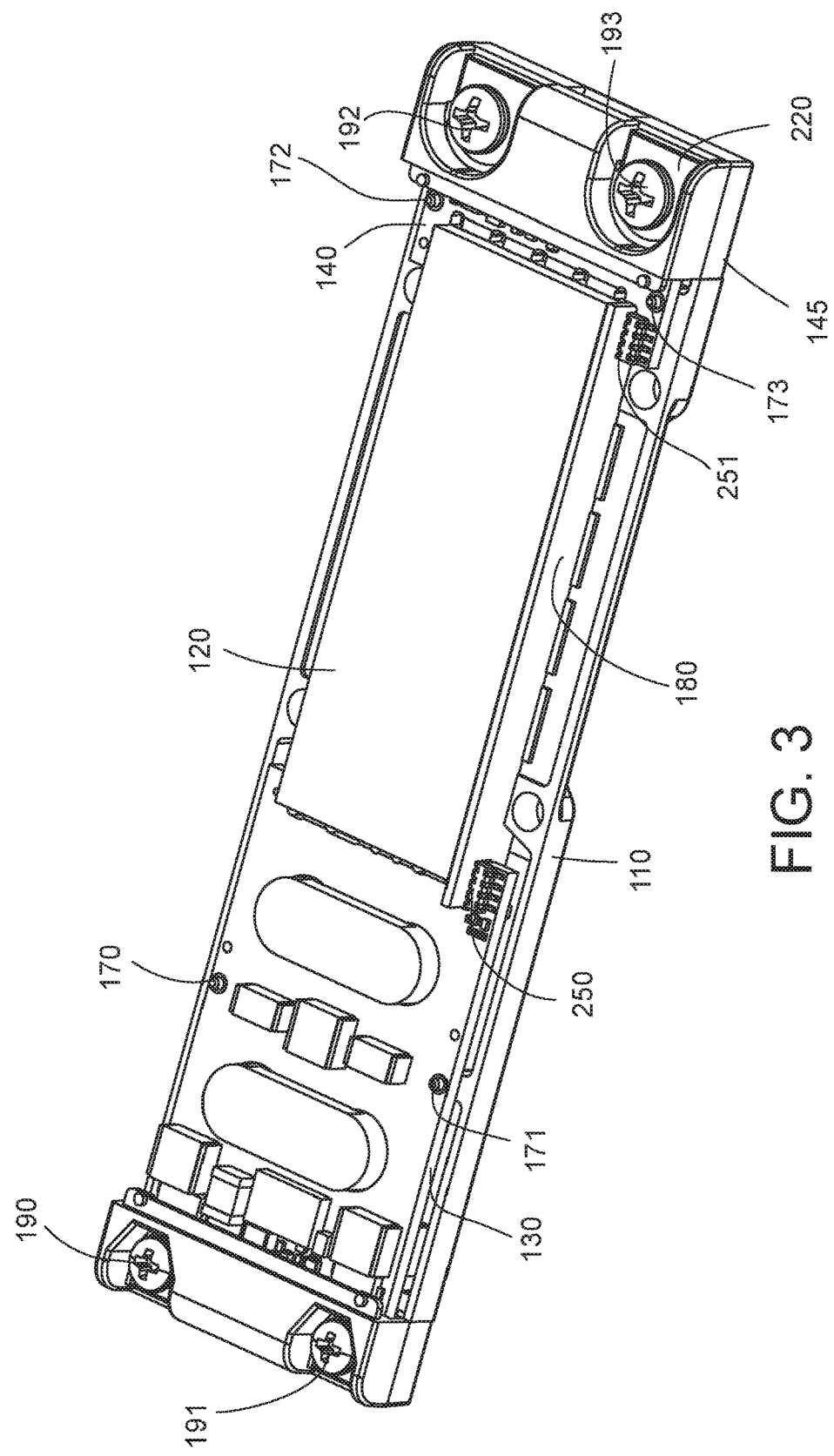
FIG. 3 shows a top perspective view of the power adapter of FIG. 1 with a top cover removed.

FIGS. 2 and 3, respectively show an exploded perspective view of the power adapter 10 of FIG. 1 and a perspective view of the assembled power adapter 10 with the top cover removed. As illustrated in FIGS. 1, 2 and 3, the power adapter 10 may comprise a top cover 100; a bottom cover 110; an input circuit board 130; an output circuit board 140; an input end-cap 135 and associated input termination hardware 190, 191, 194, 195; an output end-cap 145 and associated output termination hardware 192, 193, 196, 197; a power conversion module 120; and a bridge board 180. Insulators (e.g., insulators 150, 151, 152, 153) may provide electrical insulation between conductors and components on a circuit board (e.g., circuit boards 130, 140) and covers 100, 110. Bonding material 160, 161 may provide a mechanical and/or thermal connection between the top and bottom surfaces of the power conversion module 120 and the adjacent interior surfaces of the top and bottom covers 100, 110.

Figure 4:
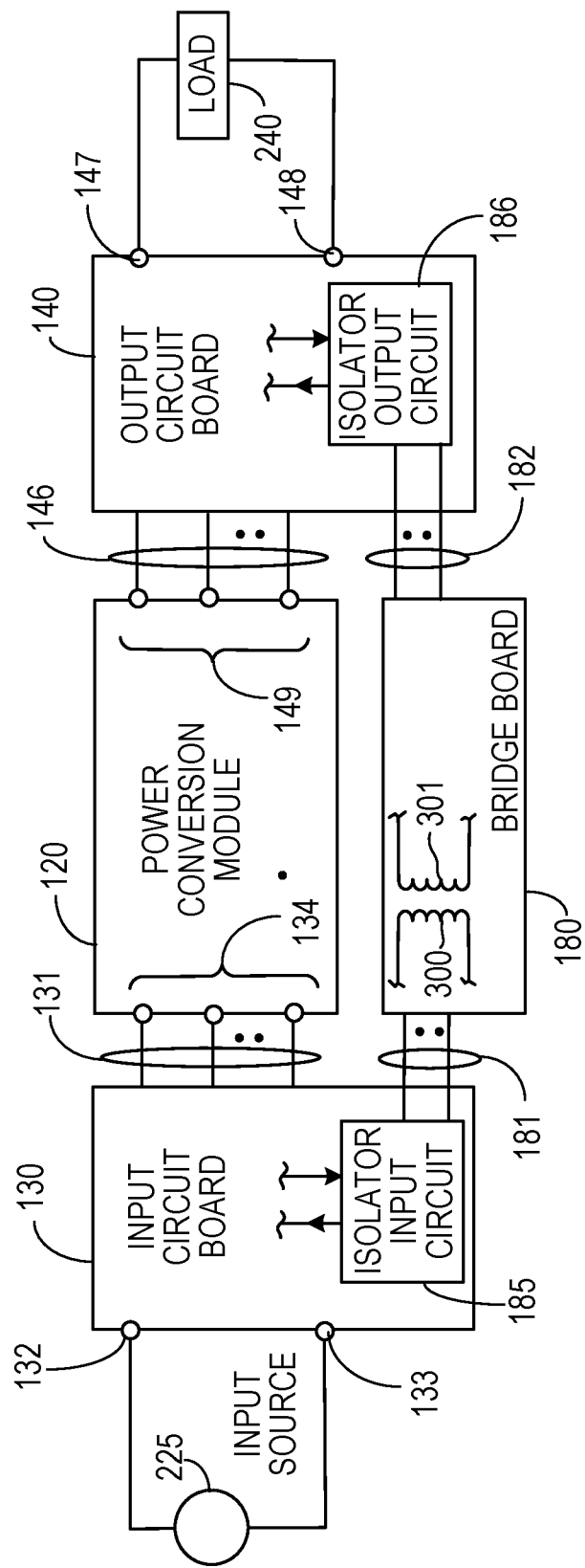
FIG. 4 is a schematic of an embodiment of a power adapter.

A schematic diagram of an embodiment of the power adapter 10 is shown in FIG. 4. An input circuit board 130 receives power at input terminals 132, 133 from an input source 225 and delivers power, via connections 131 (which may also comprise unidirectional or bidirectional input control and signal lines) to input terminals 134 on the power conversion module 120. The output circuit board 140 receives power from output terminals 149 of the power conversion module 120 via connections 146 (which may also comprise unidirectional or bidirectional output control and signal lines) and delivers power, via output terminals 147, 148 to the load 240. The input circuit board 130 may comprise a variety of components and circuits (not shown) for processing and filtering power received from the input source 225 (e.g., noise and transient filtering circuitry, rectification circuitry, fuse circuitry, power factor correction circuitry); the output circuit board 140 may comprise a variety of components and circuits for processing power received from the power conversion module 120 (e.g., noise filtering circuitry, filter capacitors, supervisory circuitry). The power conversion module may be any of a variety of isolated or non-isolated AC-DC or DC-DC converters, including power factor correcting. Additional communication and/or supervisory circuitry may be provided on the input and/or output circuit boards 130, 140.

Referring to FIGS. 3 and 4, the power adapter as shown comprises an isolator for communicating status and/or control information between the input and output sides of the power adapter 10 while preserving the galvanic isolation between the input and output. The isolator may preferably be of the bridge board kind described in Isolator with Integral Transformer, U.S. patent application Ser. No. 14/596,836, filed on Jan. 14, 2015 (the "BB Isolator Application"), incorporated here by reference. Bridge board isolators of the kind described in the BB Isolator Application may include a bridge board physically spanning the distance between the input board 130 and the output board 140 and in which are formed isolation transformers. The bridge board provides communication and interconnection between the input and output boards while preserving the galvanic isolation between the two. As described in the BB Isolator Application, the isolator circuitry may be located on the bridge board or the input and output boards. In the example shown in FIG. 4, the isolator input circuitry 185 (FIG. 4) is located on input circuit board 130, and the isolator output circuitry 186 (FIG. 4) is located on output circuit board 140. A bridge board 180, comprising one or more transformers including pairs of magnetically coupled windings (e.g., magnetically coupled windings 300, 301, FIG. 4), spans a distance between the input circuit board 130 and the output circuit board 140. As described in the BB Isolator Application, the bridge board 180 may comprise multiple substrate layers, with magnetically coupled windings arranged on separate layers, the substrate material providing galvanic isolation between the windings. Other layers on the bridge board may comprise conductive shields, as also described in the BB Isolator Application.

Figure 5:
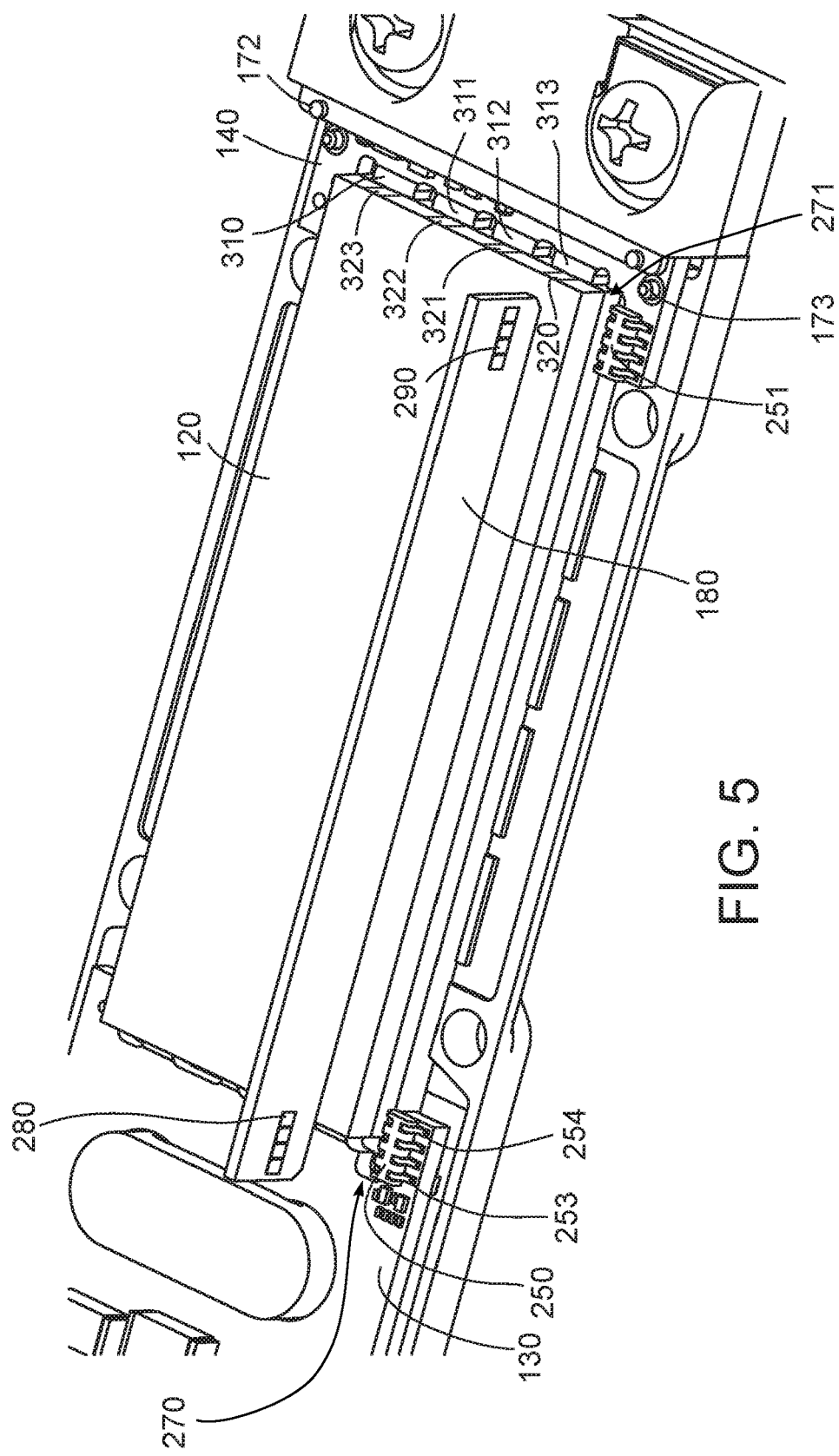
FIG. 5 shows a partially exploded top perspective view of the power adapter of FIG. 1 with a top cover removed.
Figure 6:
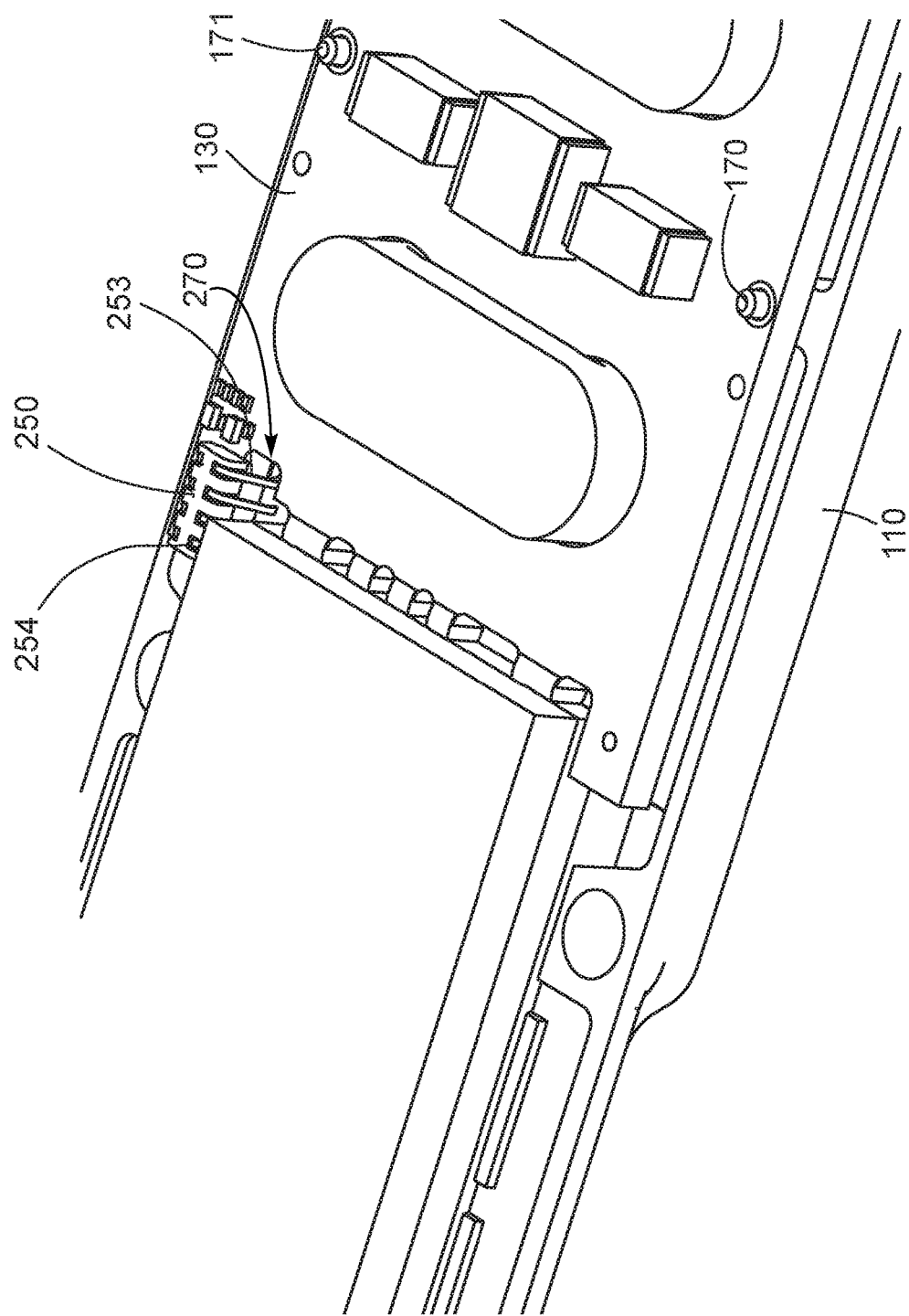
FIG. 6 shows a top perspective view of a portion of the power adapter of FIG. 1 with the top cover and a bridge board removed.
Figure 7:
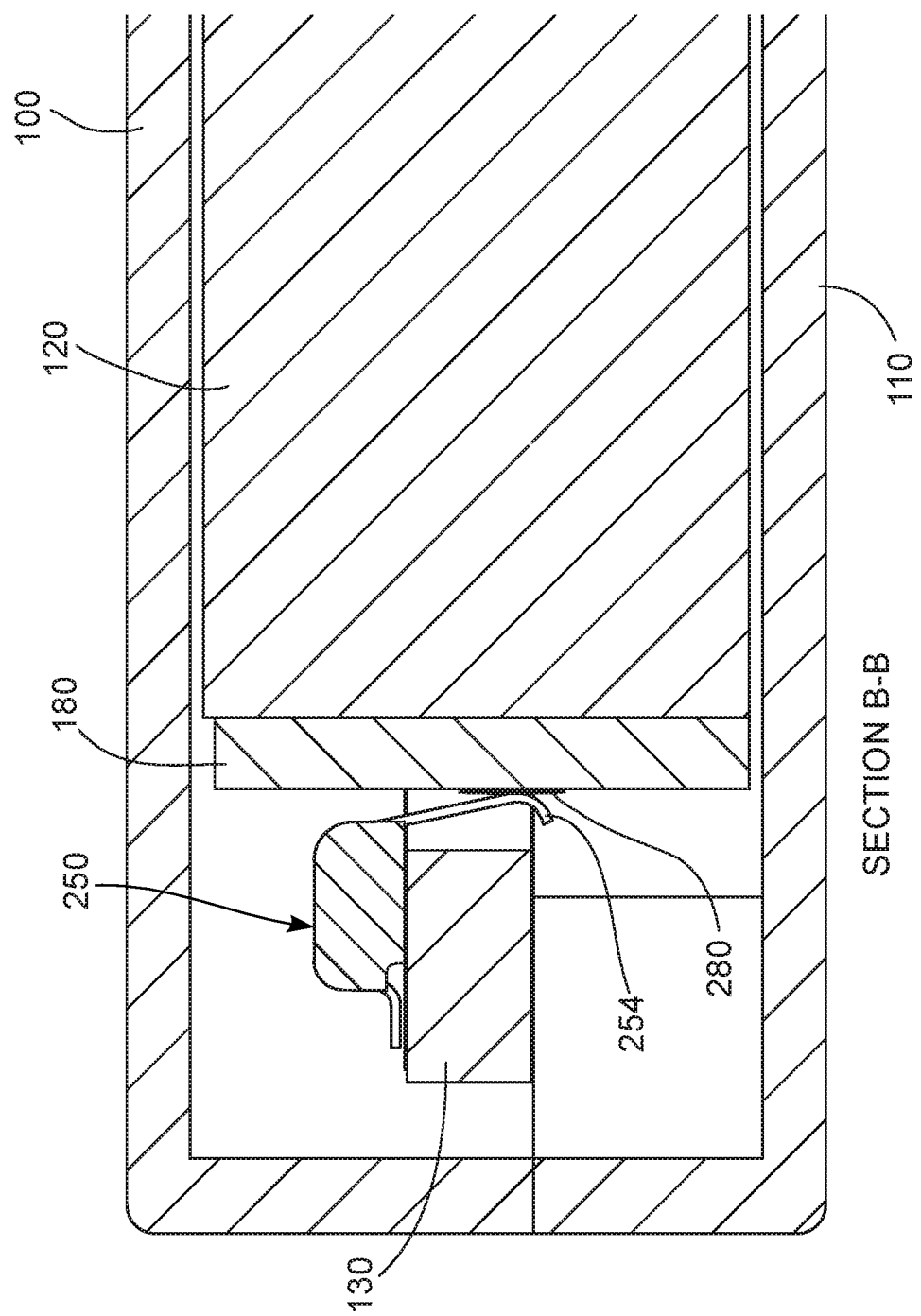
FIG. 7 shows a section through the power adapter of FIG. 1.
Figure 8:
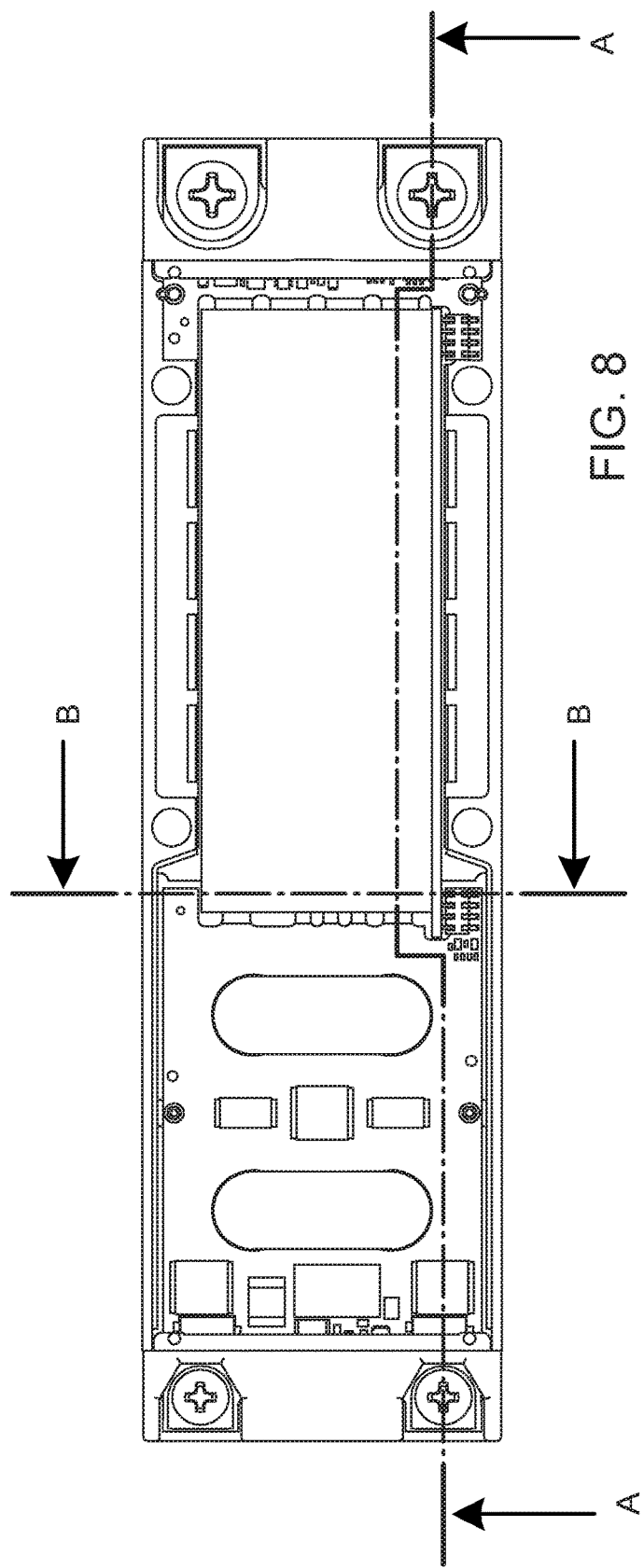
FIG. 8 shows locations of the sectional views of FIGS. 7 and 10.

As described in the BB Isolator Application, the connections between the bridge board 180 and the input and output boards 130, 140 may be removable. FIG. 5 shows a partially exploded top perspective view of the power adapter 10 with the bridge board 180 in a position above the converter prior to installation; FIG. 6 shows a partial perspective view of the converter with the bridge board removed; FIG. 7 shows a section, B-B, through a portion of the converter; FIG. 8 shows the location of the section B-B. As shown in FIGS. 5, 6 and 7, the bridge board 180 comprises conductive pads (e.g., pads 280, 290) that connect to the ends of the transformer windings (i.e., windings 300, 301). Connections between the input board 130 and output board 140 and the bridge board 180 are made by means of connectors 250, 251, which comprise contacts (e.g., contacts 253, 254, FIGS. 5-7) that align and make contact with bridge board pads (e.g., pads 280, 290). As shown in FIG. 5, alignment features (e.g., slot 270, edge location 271) may be provided to ensure proper alignment between the contacts and the pads.

Figure 9:
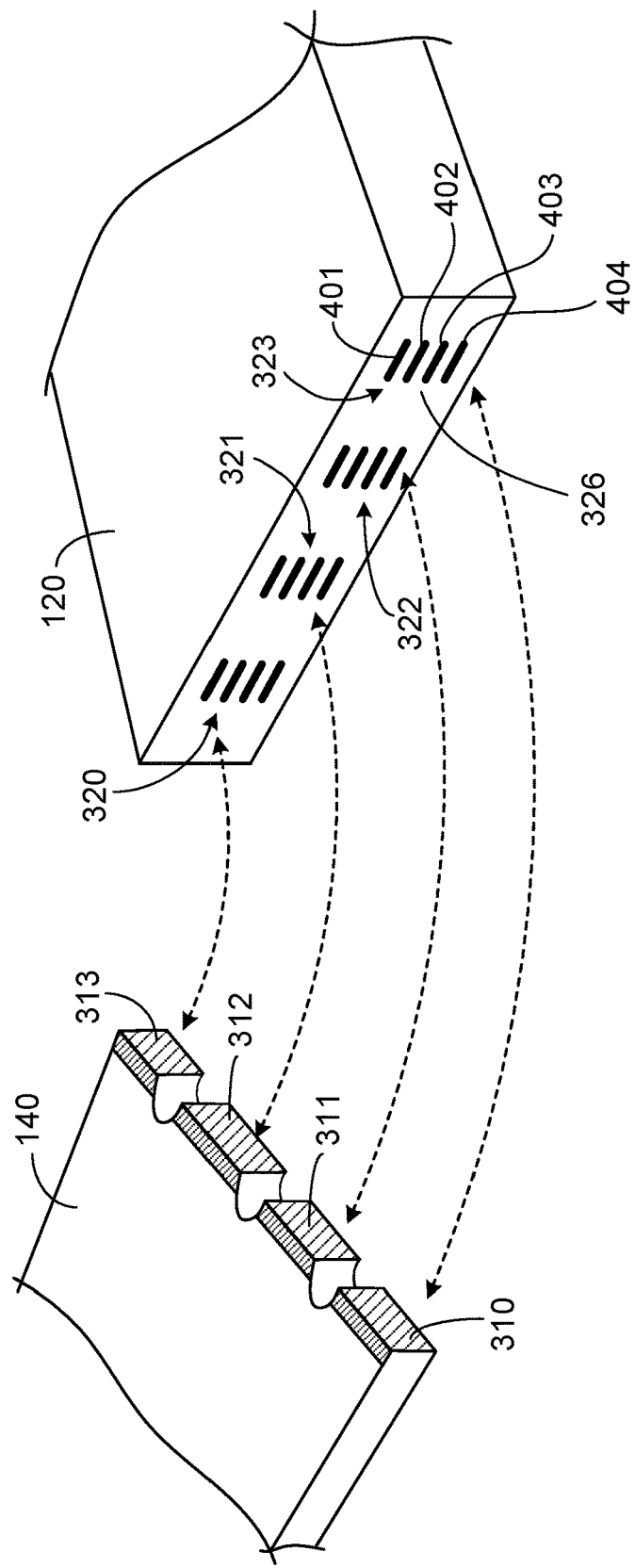
FIG. 9 shows a diagram of a method for connecting a substrate to a module.

The power conversion module 120 as shown in FIGS. 2-10 may be encapsulated for example as described in Vinciarelli et al, Panel-Molded Electronic Assemblies, U.S. patent application Ser. No. 14/116,642, filed on Nov. 8, 2013, (the "Panel Mold Application") (assigned to VLT, Inc. of Sunnyvale, Calif., the entire disclosure of which is incorporated herein by reference). Such "panel molded" power conversion modules may have electrical contact regions located at mid-elevation along vertical edges of the encapsulated module for making electrical connections to the power conversion circuitry inside the module. A power conversion module 120 of the type described in the Panel Mold Application is shown in FIGS. 5 and 9 comprising contact regions 320-323 located on a vertical edge (e.g., vertical edge 326, FIG. 9) that spans from the top and bottom surfaces of the power conversion module. The contact regions of the module may, as described in the Panel Mold Application, be formed by exposing portions of conductive traces or features (e.g., etches 401-404) at the edges of multiple layers of a circuit board contained within the module 120. Each group of exposed features, which together form a single contact node, may be referred to as a bar code. In FIG. 9, four bar codes, 320, 321, 322, 323, are shown each having four exposed conductive features. Although the contact regions, e.g. 320, 321, 322, 324, are shown as bar codes in FIG. 9, some or all may be formed as continuous conductive regions and although shown as occupying only a portion of the height of the vertical edge and being located at mid elevation in the figures, one or more of the contact regions may extend beyond the mid-elevation location to the top or bottom surfaces or both of the power conversion module 120.

Electrical connections 131, 146 between the power conversion module 120 and the input and output boards 130, 140 may be made in a variety ways, including wires, straps, connectors, solder, conductive epoxy, and adapters such as those described in the Panel Mold Application. One approach includes direct solder connections between the input or output board and the power converter module 120. For example as shown in the cross section view of FIG. 10 (which shows a section through the power adapter 10 along the line A-A shown in FIG. 8), the input and output boards may be positioned at a mid-elevation, i.e., between the top and bottom surfaces of the power conversion module 120, and arranged end-to-end with the module 120. The mid-elevation position of the input and output boards and the mid-elevation connections between the boards and the power conversion module 120 may be established even in the case where some or all of the contact regions on the power conversion module 120 extend to the top or bottom surfaces or both, i.e. over the entire height of the vertical edge of the power converter. Greater detail of the connections 146 between the output board 140 and the power conversion module 120 are shown in FIGS. 5 and 9. Similar connections 131 may be made between the input board 130 and the power conversion module 120. Referring to FIG. 5, one or more conductive pads, e.g., pads 310-313 located on a vertical edge of the output board 140, may be arranged to match corresponding conductive contact regions, e.g., output contact regions 320-323 on the power conversion module 120.

Solder connections between the conductive pads, e.g., pads 310, 311, 312, 313 on output board 140, and the corresponding conductive contact regions, e.g., output contacts 320, 321, 322, 323 on the module 120, may be formed, preferably at mid-elevation, for example by positioning the input 130 and output 140 boards at mid-elevation relative to the power conversion module 120 with the pads aligned with the contact regions, placing solder preforms (not shown) over the conductive pads 310, 311, 312, 313, and reflowing the solder between the pads and contact regions to form soldered joints. Preferably the conductive contact regions on the module 120, e.g., contact regions 320, 321, 322, 323, comprise 3D bar codes of the type described in Vinciarelli et al, Electronic Assemblies Having Components With Edge Connectors, U.S. patent application Ser. No. 14/596,914, filed on Jan. 14, 2015 (the "3D Bar Code Application," assigned to VLT, Inc. of Sunnyvale, Calif., the entire disclosure of which is incorporated herein by reference) for creating more robust solder joints with the input and output boards.

The pads, e.g., 310-313, and the contact regions, e.g., 320-323, may also be connected by other methods, e.g., use of conductive epoxy. Other ways to connect a board to a module include, e.g., providing input and output termination pins on the power conversion module and soldering the pins into corresponding plated holes, or a corresponding connector, in a respective input or output board.

Figure 10:
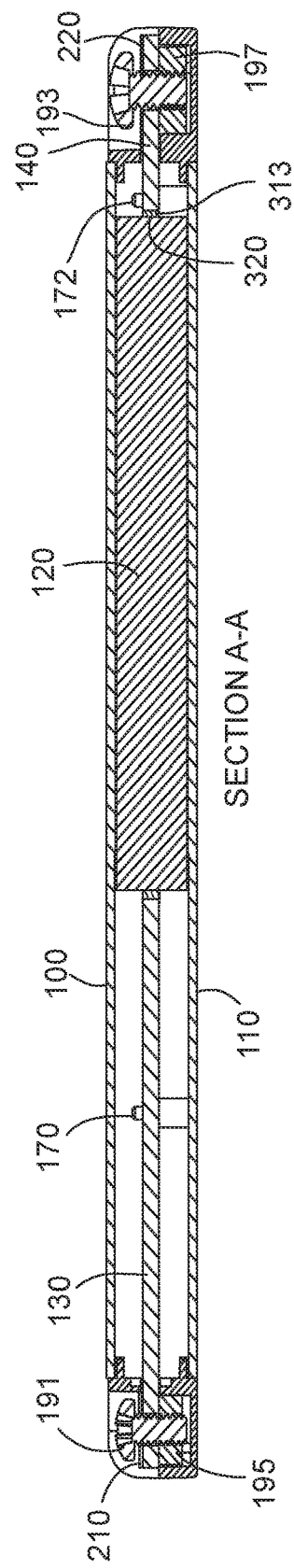
FIG. 10 shows a section through the power adapter of FIG. 1.

Referring to FIGS. 1, 2, 3 and 10, the power adapter 10 may be provided with end cap assemblies for making external connections, e.g., input connections 132, 133 (FIG. 4) and output connections 147, 148 (FIG. 4) between the power adapter and external circuitry such as the input source 225 and load 240 (FIG. 4). As shown, the input end cap assembly may comprise an insulating body 135 (e.g., made of plastic), termination screws 190, 191, and threaded nut plates 194, 195. As shown in FIGS. 2 and 10, installation of the input end cap comprises installing the threaded nut plates 194, 195 into recesses in the insulating body 135, installing the insulating body (with the nut plates installed) over the end of input board 130, and installing the termination screws 190, 191 into the nut plates 194, 195 through a hole located in the input board. Terminals 190, 191 which mate with pads 211, 210 on the input board 130 may be used to provide power connections 132, 133 (FIG. 4) for connecting the input circuitry to the source. Similarly, terminals 193, 192 which mate with pads 220, 221 on the output board 140 may be used to provide power connections 147, 148 (FIG. 4) between the output circuitry and the load 240.

Figure 14:
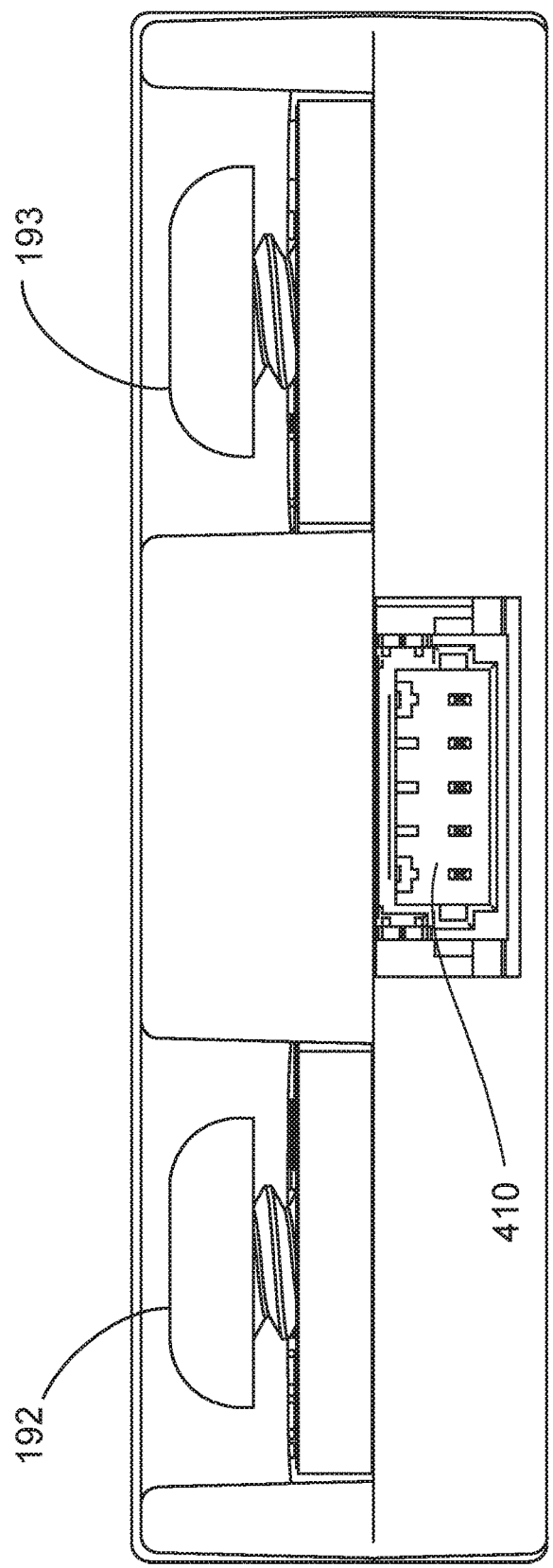
FIG. 14 shows an end cap with screw terminals and a multi-pin connector.
Figure 15:
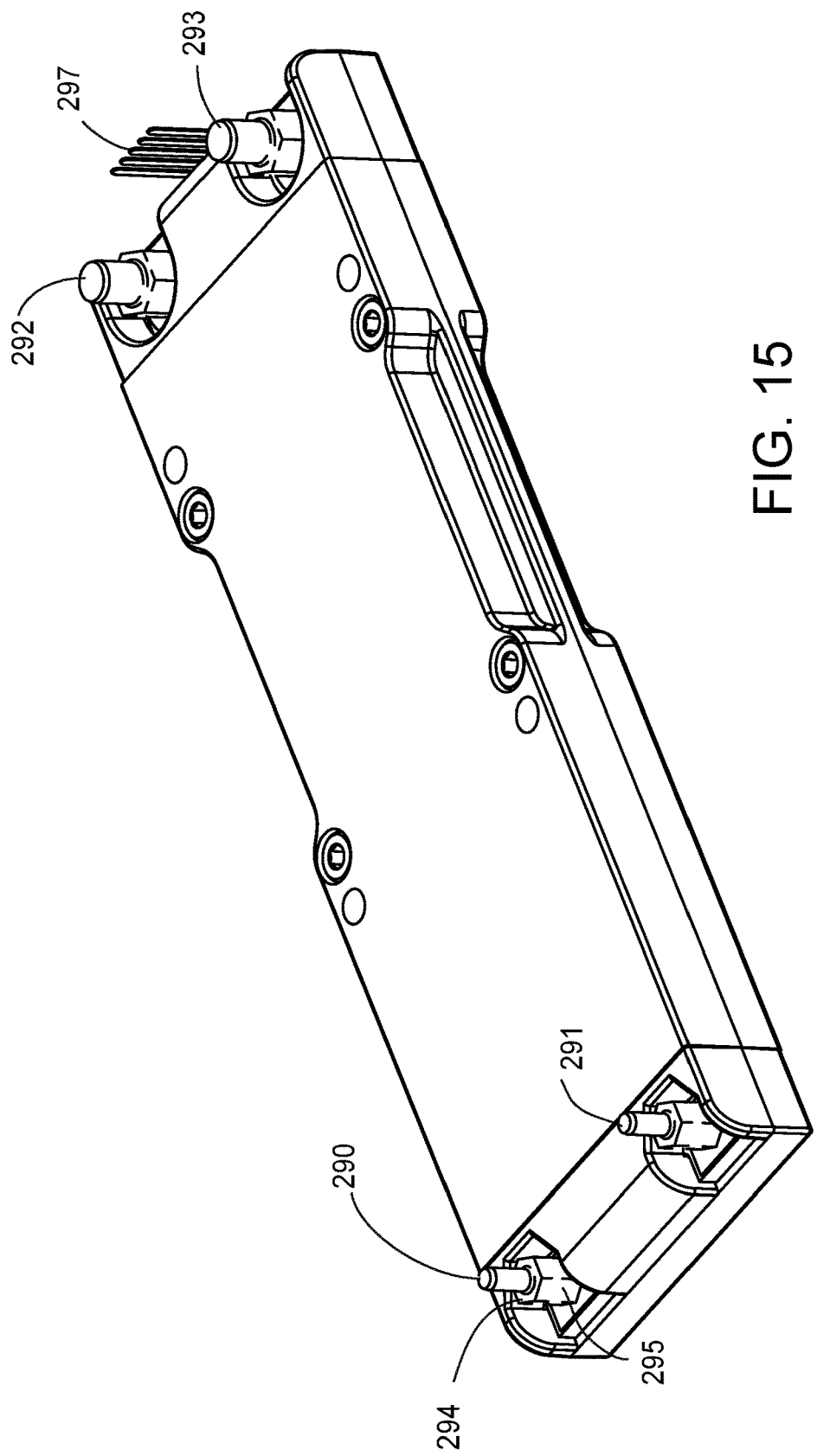
FIGS. 15 and 16 show an adapter configured for through hole mounting.
Figure 16:
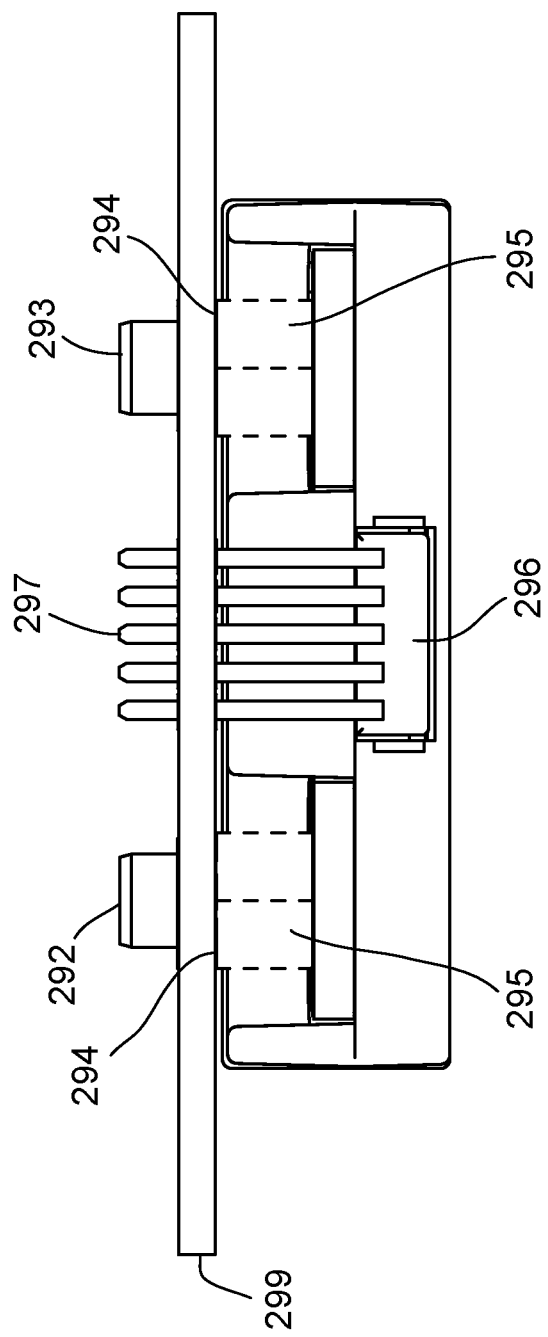

The end cap assembly may comprise other kinds of terminations either instead of, or in combination with, the threaded screw and nut plate configuration shown in the FIGS. 1-10. Terminations may be provided as additional power terminals or signal connections. FIG. 11 shows two different arrangements of pins 400, 401 that may be used for solder connections or for mating with respective terminations on a printed circuit board (e.g., plated holes or a mating connector). FIG. 12 shows an end cap configured with a multi-pin connector 410 that mates with an external connector 412. FIG. 13 shows an end cap assembly that, in addition to the screw terminals discussed above, incorporates pins 420 that mate with terminations (i.e., plated holes 430) in a printed circuit board 450. FIG. 14 shows an end cap having screw terminals, 192, 193, for making power connections to the adapter and a multi-pin connector 410 adapted to mate with a signal connector, such as the connector 412 shown in FIG. 12, for mating the control signal connections to the adapter. As shown in FIGS. 15 and 16, the end caps may have conductive posts 290, 291, 292, 293 instead of the screw terminals, 190, 191, 192, 193 shown in FIGS. 1-3. The conductive posts 290, 291, 292, 293 may include hexagonal base sections 295 to facilitate threaded engagement with nuts, e.g. nuts 194-197 (FIGS. 2, 10) in the end caps and shoulders 294 for spacing or support against an external printed circuit board. As shown in FIG. 16, a set of leads 297 may be mated via connector 296 with or replace the multi-pin connector 410 to provide a through-hole mounting option for the adapter onto an external printed circuit board, e.g., printed circuit board 299.

Because the power adapter may be specified to operate over a range of temperatures (e.g., 0 to 85 degrees Centigrade), steps may need to be taken to minimize mechanical stresses caused by differences in the coefficients of thermal expansion of the power conversion module and the cover material, e.g., to protect the integrity of the solder connections between the input or output boards and the power conversion module or other components or features. One way to reduce the stresses associated with thermal expansion is to choose a cover material having a coefficient of thermal expansion (CTE) that is approximately equal to the CTE of the power conversion module. For example, an encapsulated power conversion module marketed as VI Chip brand CHiPs manufactured by Vicor Corporation, Andover, Mass., USA, www.vicorpower.com, may have a CTE of approximately 17 ppm-per-degree-C making C14700 copper, which also has a CTE of 17 ppm-per-degree-C, a suitable choice of housing material for the CHiP.

Another way to reduce thermal stress on selected portions of the assembly such as solder connections between the input or output board and the power conversion module is to force the module and the covers to thermally expand and contract in substantially equal amounts along the length of the adapter (i.e., in a direction between the input and output of the adapter) for example by mechanically bonding the two components with a bonding material such as bonding material 160, 161 shown in FIG. 2 or with hardware. A suitable two component epoxy compound, such as Master Bond EP37-3FLFAO manufactured by Master Bond, Hackensack, N.J., USA, www.masterbond.com, may be applied in a pattern to provide a thin, continuous film of coverage between the top and bottom surfaces of the power conversion assembly 120 and the interior surfaces of the top and bottom covers 100, 110 for the bonding material 160, 161 as shown in FIG. 2.

Another way of managing thermal stress is to "pre-stress" the system by assembling it at a build temperature that is selected to pre-bias the mechanical stress between the PCM and the housing. For example, the build temperature may be near the middle of a specified temperature range to provide balanced compressive and pulling stress minimizing the differences in expansion and contraction. Alternatively, the build temperature may be near a high (or low) end of a specified temperature range to pre-bias the stress toward pulling (or compressive) stress.

The power adapter 100 shown in FIGS. 1-10 may be assembled using the following steps: the populated input 130 and output 140 boards may be assembled to their respective end cap assembly 135, 145; the bottom housing 110 may be prepared with insulators 151 and pins 170, 171, 172, 173; appropriate bonding materials may be applied to the bottom housing in the areas where the end caps will be bonded; the end caps 135, 145 may be placed onto the bottom housing 110 allowing the locating pins 170-173 to pass through respective holes in the PCBs; if necessary, the bottom portions of the magnetic cores may be placed before the input board is installed into the housing; an appropriate bonding material, such as a flexible and/or thermally conductive epoxy may be applied to the appropriate portion of the bottom housing for securing the power converter; the power converter may be placed into the bottom housing; the adhesives (structural epoxy and thermally conductive adhesive) may be cured if necessary; flux may be applied to the relevant conductive areas on the PCBs, e.g., near where the pins 170-173 and the power converter terminals will be soldered to the board; solder preforms may be placed on the PCBs adjacent the power converter terminals and the pins after which the solder may be reflowed. The insulators 152, 153, bridge board 180, and if necessary top portion of the cores, may be installed onto the bottom assembly before the top cover is installed. The top cover 100 may be prepared with insulator 158 and positioned onto the bottom assembly after a suitable adhesive such as a structural epoxy or thermally conductive adhesive is applied to the relevant surface areas on the end caps 135, 145, on the power converter 120, and on the bottom housing 110 where each mates with the top cover after which the adhesives may be cured if necessary.

Although the Figures show an embodiment in which the bridge board 180 is aligned at an essentially right angle to the input and output boards and the power conversion module allowing for a compact assembly, it should be understood that the bridge board may be installed at any angle relative to other boards and components.

FIG. 9 shows conductive pads 310-313 located on the vertical edge of the output board 140, and output contacts 320-323 located on the vertical edge 326 of the power conversion module 120. The edge of the output board 140 and the edge of the power conversion module 120 do not have to be exactly perpendicular to the top and bottom surfaces of the output board 140 and power conversion module 120, respectively, as long as the edges are approximately parallel to each other so that a good solder connection can be achieved. FIG. 3 shows the power conversion module 120 coupled to the input and output circuit boards. The internal printed circuit boards of the power conversion module 120 do not have to be exactly parallel to the input circuit board 130 and the output circuit board 140. The coefficient of thermal expansion (CTE) of the power conversion module does not have to be exactly equal to the CTE of the cover. In some implementations, the input circuit board 130 and the output circuit board 140 can be connected together to form an integral piece. For example, the input circuit board 130 and the output circuit board 140 can be portions of a single printed circuit board.

Figure 17:
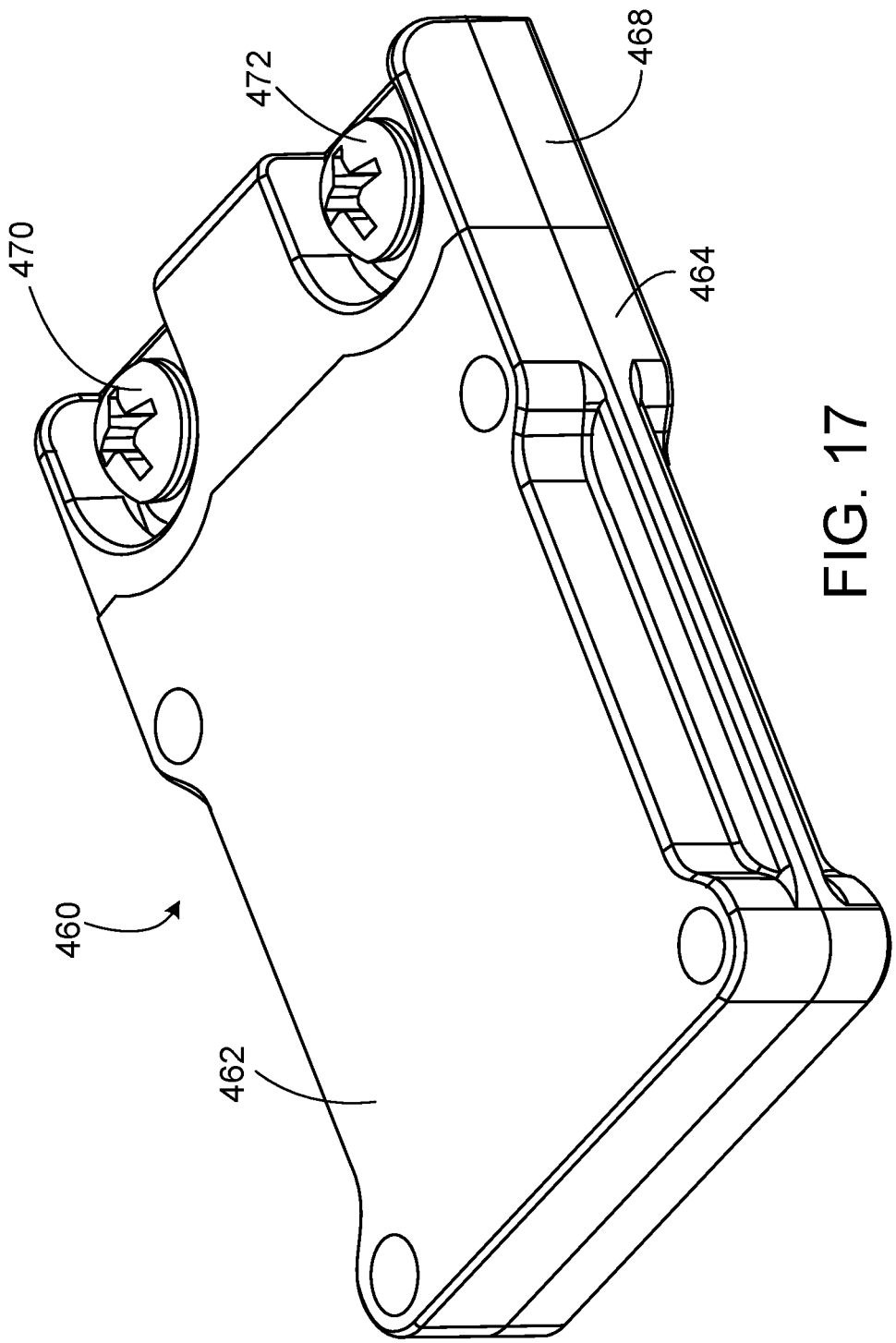
FIG. 17 is a diagram of a perspective view of an assembled power adapter.
Figure 18:
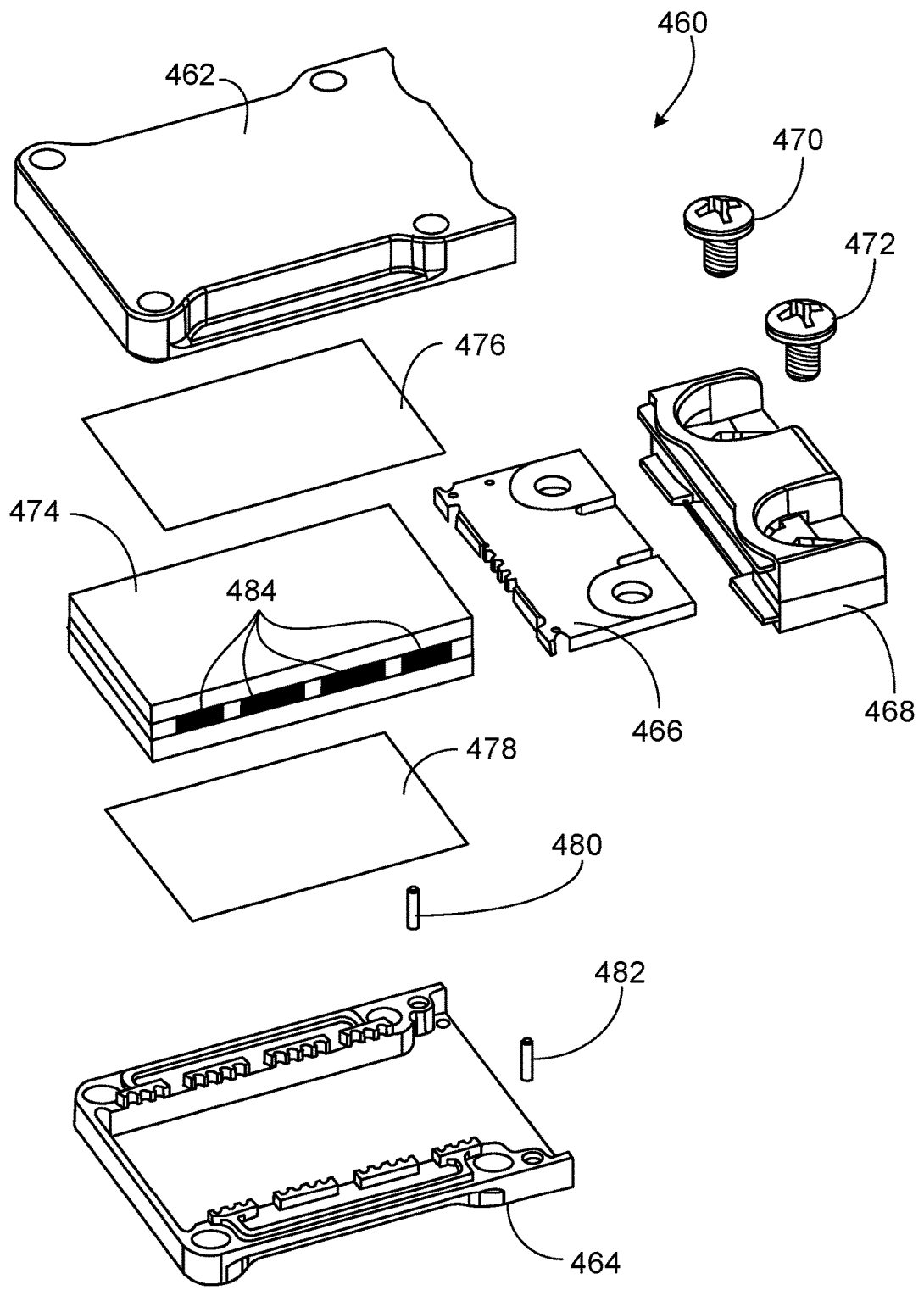
FIG. 18 shows an exploded perspective view of the adapter of FIG. 17.
Figure 19:
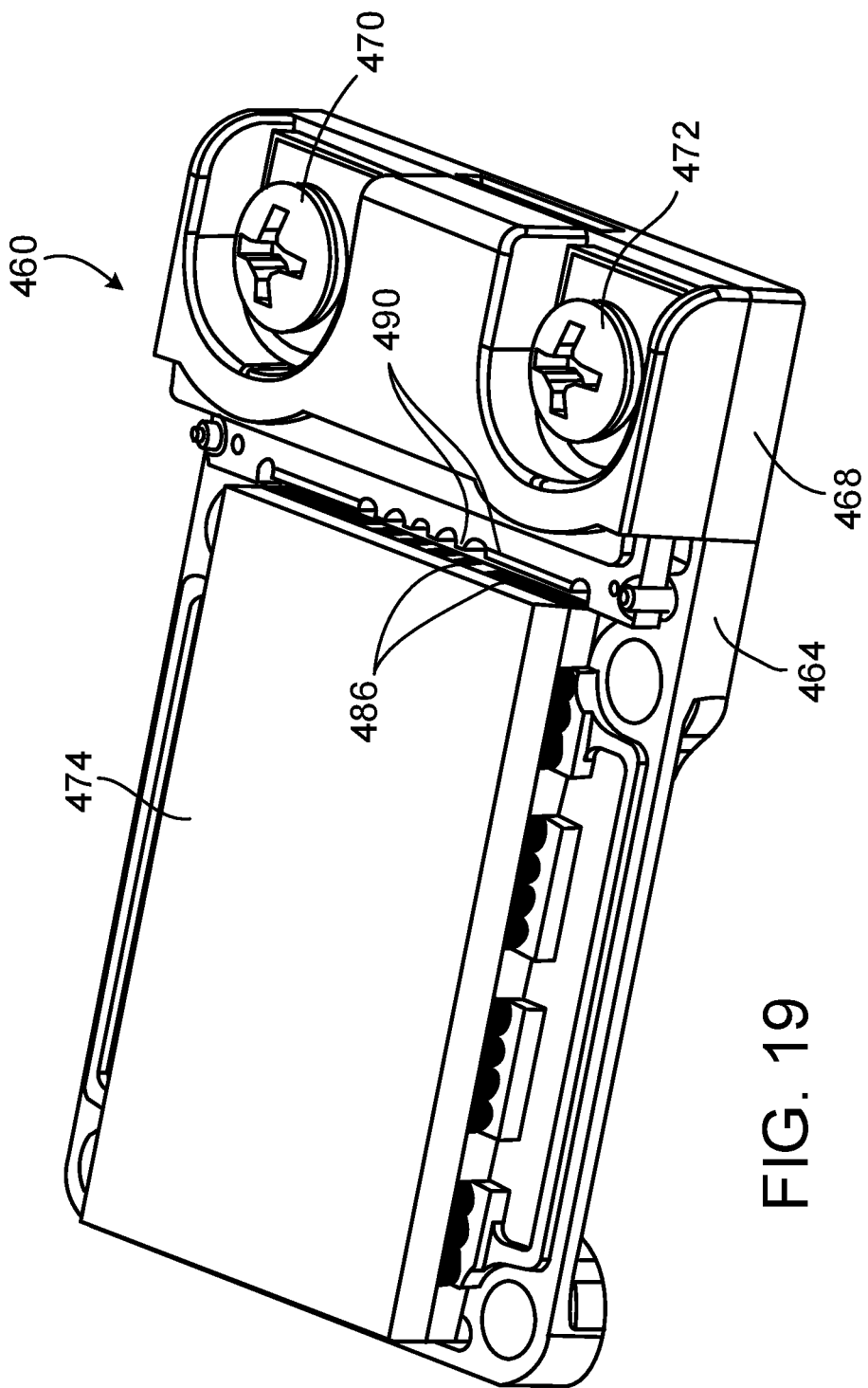
FIG. 19 shows a top perspective view of the power adapter of FIG. 17 with a top cover removed.

Referring to FIG. 17, in some implementations, a power adapter 460 may be packaged in a way such that input and output connectors (or terminals) are positioned at one end of the package (in contrast to the double-ended package shown in the example of FIG. 1). This package is useful for three-terminal designs in which there is an input, an output, and a ground (the case). Similar to the adapter 10 in FIG. 1, the adapter 460 in FIG. 17 may, e.g., receive an input from an AC and/or DC electrical source (not shown) and may deliver an output to a load (also not shown); the output may be regulated and/or scaled in magnitude relative to the input. FIGS. 18 and 19, respectively show an exploded perspective view of the power adapter 460 of FIG. 17 and a perspective view of the assembled power adapter 460 with the top cover removed. As illustrated in FIGS. 17, 18 and 19, the power adapter 460 may include a top cover 462, a bottom cover 464, an input/output circuit board 466, an end-cap 468 and associated input termination hardware 470 and output termination hardware 472, and a power conversion module 474. The top cover 462 and the bottom cover 464 may be made of metal. Bonding material 476, 478 may provide a mechanical and/or thermal connection between the top and bottom surfaces of the power conversion module 474 and the adjacent interior surfaces of the top and bottom covers 462, 464. Pins 480 and 482 are provided for use in assembling the package.

The power conversion module 474 may have contacts 484 along the two long sides of the power conversion module 474 (in this example, there are 4 contacts on each side). The contacts 484 are soldered to the metal bottom cover 474 for ground connections and also help conduct heat from the power conversion module 474 to the metal housing (top and bottom covers 462, 464). On the input/output circuit board 466 there may be mounted ancillary circuitry and any supervisory circuitry which is not shown in the drawings.

The power conversion module 474 has contact regions 486 located on a vertical edge 488 facing the end-cap 468. The contact regions 486 are arranged to match corresponding pads 490 on the input/output circuit board 466. The contact regions 486 and the pads 490 provide signal paths between the power conversion module 474 and the input/output circuit board 466.

Other embodiments are within the scope of the following claims. For example, the input and output boards and the substrate within the power conversion module may be embodied as a multilayer fiberglass printed circuit board, as a multilayer ceramic substrate, or some combination thereof. An epoxy impregnated pad may be used for the bonding material 160, 161. End cap terminations may be configured in any of a variety of configurations. In addition to or instead of the mechanical bond provided by bonding material 160, 161, the housing covers may be held together with screws, e.g., 198, 199, 200, 201, as shown in FIG. 2, or alternatively soldered, welded, or brazed.

The invention claimed is:

1. An apparatus for converting power received from an input source for delivery to a load, comprising:
a first printed circuit board ("PCB") having one or more electrical terminations adapted for connection to the input source and one or more electrical terminations for connection to the load;
a power conversion module ("PCM") having a module input and a module output, each being electrically connected to the first PCB, and power conversion circuitry adapted to convert power between the module input and the module output;
wherein at least one of the electrical connections from the module input or module output and the first PCB comprises a solder connection formed between a conductive area located on a vertical edge of the PCB and a conductive area located on a first vertical edge of the power conversion module,
wherein the vertical edges are approximately parallel to each other and the connection is located at an elevation below a top surface and above a bottom surface of the power conversion module.

2. The apparatus of claim 1 in which the power conversion module has a second conductive area located on a second vertical edge, and a solder connection is formed between the second conductive area and a metallic case.

3. The apparatus of claim 2 in which the solder connection between the second conductive area and the metallic case is located at an elevation below a top surface and above a bottom surface of the power conversion module.

4. The apparatus of claim 1 in which the module input and the module output of the power conversion module are positioned on one side of the power conversion module.

5. The apparatus of claim 1 in which the power conversion module further comprises an internal printed circuit board having a first vertical edge including one or more surface contacts and a second vertical edge having one or more surface contacts, the first and second vertical edges forming a portion of first and second vertical edges of the power conversion module.

6. The apparatus of claim 1, further comprising an end cap assembly having a non-conductive body and a plurality of electrically conductive terminals connected to the first printed circuit board.

7. The apparatus of claim 1 in which the solder connection directly contacts the conductive area located on the vertical edge of the PCB and the conductive area located on the first vertical edge of the power conversion module.

8. The apparatus of claim 1 in which the vertical edge of the PCB comprises a perimeter edge of the PCB.

* * * * *